(12) United States Patent
Weiberth et al.

(10) Patent No.: US 7,112,682 B2
(45) Date of Patent: Sep. 26, 2006

(54) PROCESS FOR THE PREPARATION OF N-AMINO SUBSTITUTED HETEROCYCLIC COMPOUNDS

(75) Inventors: Franz Weiberth, Raritan Township, NJ (US); George Everett Lee, Somerville, NJ (US); Reda G. Hanna, Allentown, PA (US); Juergen Mueller-Lehar, Weinolsheim (DE); Silke Dubberke, Floersheim (DE); Roland Utz, Kronberg (DE)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 10/957,124

(22) Filed: Oct. 1, 2004

(65) Prior Publication Data

US 2005/0101654 A1    May 12, 2005

Related U.S. Application Data

(60) Provisional application No. 60/508,335, filed on Oct. 3, 2003.

(51) Int. Cl.
  *C07D 209/32* (2006.01)
(52) U.S. Cl. .................................................. 548/483
(58) Field of Classification Search ................ 548/440, 548/483
  See application file for complete search history.

(56) References Cited

U.S. PATENT DOCUMENTS 5,459,274 A    10/1995    Lee et al.

FOREIGN PATENT DOCUMENTS

EP          0249452        12/1987
JP          01157922        6/1989

OTHER PUBLICATIONS

Preston et al. Journal of the Chemical Society, Abstracts, 1943, 659-661. *Cas Abstact Attached.*
Somei et al. Chem. Pharm. Bull. 1978, 26, 2522-2534.*
Cao et al. Organic Letters 2002, 4(17), 2853-2856.*
Masanori Somiei et al., 1-AMINOINDOLES, Tetrahedron Letters (1974, pp. 461-462, No. 5).
A. E. Arbuzov et al., Syntheses Of Heterocyclic Compounds Based On The Fischer Reaction, Journal Of General Chemistry of the USSR (1957, pp. 2401-2412, vol. 27).
Joseph T. Klein et al., Synthesis And Structure- Activity Relationships of N-Propyl-N-(4-Pyridinyl)-1H-Indol-1-Amine (Besipirdine) and Related Analogs as Potential Therapeutic Agents for Alzheimer's Disease, J. Med. Chem. (1996, pp. 570-581, vol. 39).
Kim Andersen et al., Selective, Centrally Acting Serotonin 5-HT2 Antagonists. 2. Substituted 3-(4-Fluorophenyl)-1H-Indoles, J. Med. Chem. (1992, pp. 4823-4831, vol. 35).
Masanori Somei et al., Preparation Of N-Aminoheterocycles And Their Reactions, Pharm. Inst. Tohoku Univ., Sendai Japan (1975, pp. 219-223) abstract.
Masanori Somei et al., The Chemistry Of Indoles, Tetrahedron Letters No. (1974, pp. 3605-3608, vol. 41).

* cited by examiner

*Primary Examiner*—Joseph K. McKane
*Assistant Examiner*—Jason M. Nolan
(74) *Attorney, Agent, or Firm*—Balaram Gupta

(57) ABSTRACT

An improved process for the preparation of N-amino nitrogen heterocyclic compounds is disclosed and claimed. In an embodiment of this invention, a compound of the formula (VI) is prepared starting from the corresponding indole derivative by way of N-amination and subsequently forming an hydrazone by the reaction with a keto compound in a single step. Further reduction of the hydrazone and subsequent coupling with a pyridine compound affords the compound of formula VI or a suitable salt thereof.

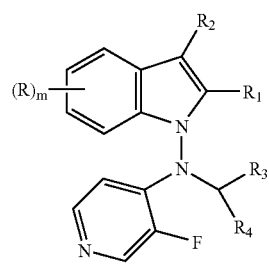

(VI)

54 Claims, No Drawings

PROCESS FOR THE PREPARATION OF N-AMINO SUBSTITUTED HETEROCYCLIC COMPOUNDS

This application claims the benefit of U.S. Provisional Application No. 60/508,335, filed Oct. 3, 2003.

BACKGROUND OF THE INVENTION

1. Field of the Invention

The present invention relates to a process of N-aminating a series of nitrogen containing heterocyclic compounds. More specifically, the present invention relates to an improved process for the preparation of N-amino-indoles by the N-amination of indoles. This invention also relates to an improved process for the preparation of N-(n-propyl)-N-(3-fluoro-4-pyridinyl)-1H-3-methyl-indol-1-amine and the product derived therefrom.

2. Description of the Prior Art

Various N-amino substituted nitrogen heterocyclic compounds have been used as intermediates in the manufacture of a variety of organic compounds, which are primarily used in pharmaceutical applications among many other uses. A class of nitrogen heterocyclic compounds of particular importance is N-amino indoles. It has been reported in the literature that the N-amination of indoles and other nitrogen heterocycles, such as carbazoles and pyrroles, can typically be performed by the portionwise addition of hydroxylamine-O-sulfonic acid (HOSA) to the indole in the presence of an excess of potassium hydroxide in a solvent such as dimethylformamide (DMF), see for example, Somei, M.; Natsume, M. *Tetrahedron Letters* 1974, 461. A similar N-amination procedure, for example, of indoles is described in U.S. Pat. No. 5,459,274, both of these references are incorporated herein by reference in their entirety.

However, the above mentioned method has several limitations and is not advantageous for the preparation of several of the N-aminoindoles especially with respect to the large scale and commercial synthesis of N-aminoindoles. For instance, the portionwise addition of the hygroscopic HOSA as a solid poses problems and is not practical. Additionally, the reaction has to be carried out under heterogeneous conditions resulting in unacceptably low yields of the product. Actually, the product yields are typically in the low levels of around 40 percent, and are often variable depending upon the surface area and quality of potassium hydroxide employed and the agitation efficiency of the reaction medium. Thus, this process is not suitable for a scale-up operation. Most importantly, generally, a large excess of the base is used thus necessitating undue waste disposal problems after neutralization and work-up of the product, thus rendering this process uneconomical for a commercial operation.

It has also been disclosed in the literature that N-amination of hexamethyleneimine can be carried out using HOSA in the presence of an aqueous solvent and an inorganic base, see for example EP Patent Application No. 0 249 452, incorporated herein by reference in its entirety. The inorganic bases disclosed therein include hydroxides of alkali metals and hydroxides of alkaline earth metals. Specifically, in this process, it is disclosed that N-amination can be carried out by simultaneous feeding of an aqueous solution of HOSA and an aqueous solution of sodium hydroxide to an aqueous solution of hexamethyleneimine. However, this process is similarly ridden with all of the disadvantages discussed hereinabove and in addition this process is specific to hexamethyleneimine, which is a stronger base than various other nitrogen heterocyclic compounds such as indoles, carbazoles, pyrroles, etc. In spite of this, the reported product yields are very low. Accordingly, there is a need for an improved process for the N-amination of nitrogen containing heterocyclic compounds.

As noted above, the N-amino nitrogen heterocyclic compounds so formed serve as useful intermediates for the formation of N-alkylamino nitrogen containing compounds, for example, N-alkylamino indoles. Generally, N-alkylation of the amino group can be carried out using an alkylating agent such as haloalkane in the presence of a base. However, such alkylation reactions often result in considerable amounts of side products resulting from the competing alkylation of the heterocyclic ring, and therefore, are not desirable, see for example U.S. Pat. No. 5,459,274. In addition, such alkylation processes also generate undue side products such as alkali halides that need to be disposed of rendering them unsuitable for an industrial scale-up operation.

Thus it is an object of this invention to provide a new homogeneous process for the N-amination of a variety of nitrogen heterocyclic compounds.

It is further an object of this invention to provide a process for the N-amination of nitrogen heterocyclic compounds involving an organic base whereby the N-amino-heterocyclic compounds are prepared in high yields and in high purity.

It is also an object of this invention to provide a new N-alkylation process which does not result in any side products thus offering high purity N-alkylamino heterocyclic compounds.

Other objects and further scope of the applicability of the present invention will become apparent from the detailed description to follow.

SUMMARY OF THE INVENTION

It has now been found that N-amination of a variety of nitrogen heterocyclic compounds can be carried out in a homogeneous medium using an organic base and an organic solvent, such as an aprotic solvent. Thus, in accordance with one aspect of the present invention, there is provided a process for the preparation of a compound of the formula II:

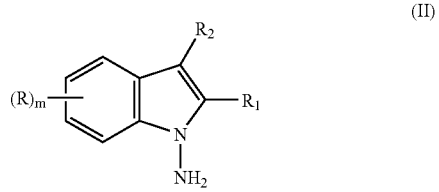

(II)

The process of this aspect of the invention comprises the following steps:

(a) In step (a), a solution of hydroxylamine-O-sulfonic acid (HOSA) is prepared in a suitable organic solvent.

(b) In step (b), a solution of a suitable base is prepared in a suitable organic solvent.

(c) In step (c), a solution of a compound of the formula I is prepared in a suitable organic solvent.

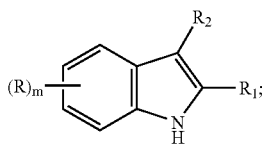

(d) Finally, in step (d), the solution prepared in step (a) and the solution prepared in step (b) are added simultaneously and proportionally to the solution prepared in step (c), which is taken in a suitable reaction vessel at a suitable reaction temperature to provide the compound of formula (II) in high purity and high yields.

Wherein:

R is hydrogen, $C_1$–$C_4$-alkyl, $C_1$–$C_4$-alkoxy, benzyloxy or fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and sum of x and y is $2n+1$;

$R_1$ and $R_2$ are the same or different and are each independently selected from hydrogen, $C_1$–$C_4$-alkyl, $C_1$–$C_4$-alkoxy, benzyloxy or fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and sum of x and y is $2n+1$; or $R_1$ and $R_2$ taken together with the carbon atoms to which they are attached form a $C_5$–$C_8$ cyclic ring; and m is 1 or 2.

In another aspect of this invention there is also provided another process for the preparation of a compound of the formula II as described herein. The process of this aspect of the invention comprises the following steps. In step (a), a solution of hydroxylamine-O-sulfonic acid and a compound of the formula I as described herein is prepared in a suitable organic solvent. In step (b), a solution of a suitable base is prepared in a suitable organic solvent. In step (c) the solution prepared in step (a) is contacted simultaneously and proportionally with the solution prepared in step (b) at a suitable reaction temperature to provide the compound of formula (II) in high purity and high yields. Wherein R, $R_1$, $R_2$, and m are as defined above.

In yet another aspect of this invention there is also provided a process for the preparation of a compound of the formula IV:

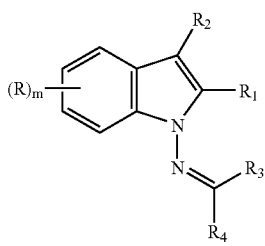

In this aspect of the invention, the process involves the following. A solution of hydroxylamine-O-sulfonic acid in a suitable organic solvent and a solution of a suitable base in a suitable organic solvent are added simultaneously and proportionally to a solution of a compound of the formula I, as described herein, in a suitable organic solvent at a suitable reaction temperature wherein the compound of the formula (I), as described herein, is taken in a suitable reaction vessel. This reaction provides a compound of the formula (II) as described herein.

The resulting N-amino-indole compound (II) is then reacted in the same reaction vessel with a compound of the formula (III):

to provide the compound of formula (IV). Wherein R, $R_1$, $R_2$, and m are as defined above, and $R_3$ and $R_4$ are the same or different and are each independently selected from hydrogen or $C_1$–$C_4$-alkyl.

Finally, in yet another aspect of this invention there is also provided a process for the preparation of a compound of the formula VI:

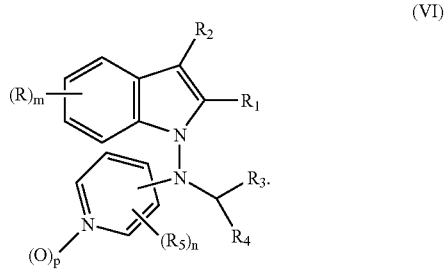

In this aspect of the invention, the process involves the following steps:

In step (a), the compound of formula (IV) as described herein is first prepared essentially following the procedures of the above mentioned embodiment. That is, a solution of hydroxylamine-O-sulfonic acid in a suitable organic solvent and a solution of a suitable base in a suitable organic solvent is added simultaneously and proportionally to a solution of a compound of the formula I in a suitable organic solvent at a suitable reaction temperature wherein the compound of the formula (I), as described herein, is taken in a suitable reaction vessel. This reaction provides a compound of the formula (II) as described herein. The resulting N-amino-indole compound (II) is then reacted in the same reaction vessel with a compound of the formula (III) to provide a compound of formula (IV).

In step (b) of this process of the invention, the compound of formula (IV) is reacted with a suitable reducing agent to provide a compound of formula (V):

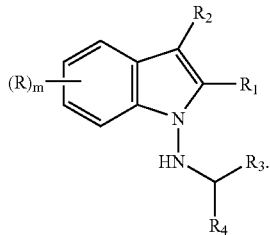

(V)

Finally, in step (c) of this process of the invention, the compound of formula (V) is then reacted with a compound of the formula (VII):

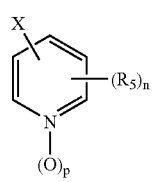

(VII)

in the presence of hydrochloric acid to provide the compound of formula (VI) as its hydrochloride. Wherein R, $R_1$, $R_2$, $R_3$, $R_4$ and m are as described above. $R_5$ is hydrogen, nitro, amino, halogen, $C_{1-4}$alkyl, $C_{1-4}$alkanoylamino, phenyl-$C_{1-4}$alkanoylamino, phenylcarbonylamino, alkylamino or phenyl-$C_{1-4}$alkylamino; X is halogen; n is 1 or 2 and p is 0 or 1.

Yet in another aspect of this invention there is also provided a compound of the formula (IV), wherein said substituents are as described herein with the proviso that when R and $R_3$ are hydrogen, $R_4$ is not hydrogen or methyl.

DETAILED DESCRIPTION OF THE INVENTION

The terms as used herein have the following meanings:

As used herein, the expression "$C_{1-4}$-alkyl" includes methyl and ethyl groups, and straight-chained or branched propyl and butyl groups. Particular alkyl groups are methyl, ethyl, n-propyl, isopropyl and tert-butyl. Derived expression such as "$C_{1-4}$-alkoxy", "phenyl-$C_{1-4}$-alkylamino", "amino-$C_{1-4}$-alkyl", "$C_{1-4}$-alkylamino", "mono- or di-$C_{1-4}$-alkylamino$C_{1-4}$-alkyl", "diphenyl-$C_{1-4}$-alkyl", "phenyl-$C_{1-4}$-alkyl", "phenylcarboyl-$C_{1-4}$-alkyl" and "phenoxy-$C_{1-4}$-alkyl" are to be construed accordingly.

As used herein, the expression "$C_{1-6}$-alkanoyl" shall have the same meaning as "$C_{1-6}$-acyl", which can also be represented structurally as "R—CO—," where R is a $C_{1-5}$-alkyl as defined herein. Additionally, "$C_{1-5}$-alkylcarbonyl" shall mean same as $Cl_{1-6}$-acyl. Specifically, "$C_{1-6}$-acyl" shall mean formyl, acetyl or ethanoyl, propanoyl, n-butanoyl, etc. Derived expressions such as "$C_{1-4}$-acyloxy", "$C_{1-4}$-acyloxyalkyl", "$C_{1-6}$-alkanoylamino", "phenyl-$C_{1-6}$-alkanoylamino" are to be construed accordingly.

As used herein, the expression "$C_{1-6}$-perfluoroalkyl" means that all of the hydrogen atoms in said alkyl group are replaced with fluorine atoms. Illustrative examples include trifluoromethyl and pentafluoroethyl, and straight-chained or branched heptafluoropropyl, nonafluorobutyl, undecafluoropentyl and tridecafluorohexyl groups. Derived expression, "$C_{1-6}$-perfluoroalkoxy", is to be construed accordingly.

As used herein, the expression "heteroaryl" includes all of the known heteroatom containing aromatic radicals. Representative 5-membered heteroaryl radicals include furanyl, thienyl or thiophenyl, pyrrolyl, isopyrrolyl, pyrazolyl, imidazolyl, oxazolyl, thiazolyl, and the like. Representative 6-membered heteroaryl radicals include pyridinyl, pyridazinyl, pyrimidinyl, pyrazinyl, triazinyl, and the like radicals. Representative examples of bicyclic heteroaryl radicals include, benzofuranyl, benzothiofuranyl, indolyl, quinolinyl, isoquinolinyl, and the like radicals.

As used herein, the expression "heterocycle" includes all of the known heteroatom containing cyclic radicals. Representative 5-membered heterocycle radicals include tetrahydrofuranyl, tetrahydrothiophenyl, pyrrolidinyl, 2-thiazolinyl, tetrahydrothiazolyl, tetrahydrooxazolyl, and the like. Representative 6-membered heterocycle radicals include piperidinyl, piperazinyl, morpholinyl, thiomorpholinyl, and the like. Various other heterocycle radicals include, without limitation, aziridinyl, azepanyl, diazepanyl, diazabicyclo[2.2.1]hept-2-yl, and triazocanyl, and the like.

"Halogen" or "halo" means chloro, fluoro, bromo, and iodo.

As used herein, "patient" means a warm blooded animal, such as for example rat, mice, dogs, cats, guinea pigs, and primates such as humans.

The term "pharmaceutically acceptable salts" as used herein means that the salts of the compounds of the present invention can be used in medicinal preparations. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, hydrobromic acid, sulfuric acid, methanesulfonic acid, 2-hydroxyethanesulfonic acid, p-toluenesulfonic acid, fumaric acid, maleic acid, hydroxymaleic acid, malic acid, ascorbic acid, succinic acid, glutaric acid, acetic acid, salicylic acid, cinnamic acid, 2-phenoxybenzoic acid, hydroxybenzoic acid, phenylacetic acid, benzoic acid, oxalic acid, citric acid, tartaric acid, glycolic acid, lactic acid, pyruvic acid, malonic acid, carbonic acid or phosphoric acid. The acid metal salts such as sodium monohydrogen orthophosphate and potassium hydrogen sulfate can also be formed. Also, the salts so formed may present either as mono- or di-acid salts and can exist either as hydrated or can be substantially anhydrous. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The expression "stereoisomers" is a general term used for all isomers of the individual molecules that differ only in the orientation of their atoms in space. Typically it includes mirror image isomers that are usually formed due to at least one asymmetric center, (enantiomers). Where the compounds according to the invention possess two or more asymmetric centers, they may additionally exist as diastereoisomers, also certain individual molecules may exist as geometric isomers (cis/trans). Similarly, certain compounds of this invention may exist in a mixture of two or more structurally distinct forms that are in rapid equilibrium, commonly known as tautomers. Representative examples of tautomers include keto-enol tautomers, phenol-keto tautomers, nitroso-oxime tautomers, imine-enamine tautomers, etc. It is to be understood that all such isomers and mixtures thereof in any proportion are encompassed within the scope of the present invention.

In a broad sense, the term "substituted" is contemplated to include all permissible substituents of organic compounds. In a few of the specific embodiments as disclosed herein, the term "substituted" means substituted with one or more substituents independently selected from the group consisting of $C_{1-6}$alkyl, $C_{2-6}$alkenyl, $C_{1-6}$perfluoroalkyl, phenyl, hydroxy, —$CO_2H$, an ester, an amide, $C_1$–$C_6$alkoxy, $C_1$–$C_6$thioalkyl, $C_1$–$C_6$perfluoroalkoxy, —$NH_2$, Cl, Br, I, F, —NH-lower alkyl, and —N(lower alkyl)$_2$. However, any of the other suitable substituents known to one skilled in the art can also be used in these embodiments.

Thus in accordance with the practice of one aspect of this invention there is provided a process for the preparation of a variety of N-amino substituted heterocyclic compounds. Thus in a broad aspect of this invention any nitrogen heterocyclic compound of the formula (IA) can be used to prepare the corresponding N-amino-heterocyclic compounds as shown in Scheme 1.

Scheme 1

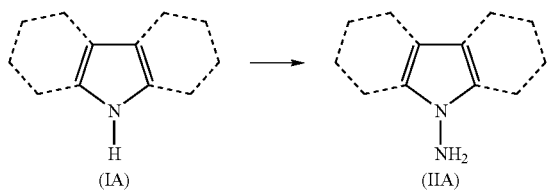

(IA)        (IIA)

Representative examples of monocyclic nitrogen heterocyclic compounds of formula (IA) that can be employed in the process of this invention include, without any limitation, substituted or unsubstituted pyrrole, pyrazole, imidazole, 1,2,3-triazole, 1,2,4-triazole and the like. Representative examples of bicyclic nitrogen heterocyclic compounds of formula (IA) that can be employed in the process of this invention include, without any limitation, substituted or unsubstituted, indole, 4, 5, 6 or 7-aza-indole, purine, indazole, 4, 5, 6 or 7-aza-indazole, benzimidazole, 4,7-diazaindole and various other isomeric diazaindoles, and the like. Representative examples of tricyclic nitrogen heterocyclic compounds of formula (IA) that can be employed in the process of this invention include, without any limitation, substituted or unsubstituted, carbazole or various known hetero atom substituted carbazoles. As defined hereinabove, any of the possible substituents can be used in the case of above mentioned substituted heterocyclic compounds provided such substituents are not interfered with the process of this invention.

Thus in a specific embodiment of this invention there is provided a process for the preparation of a compound of the formula II:

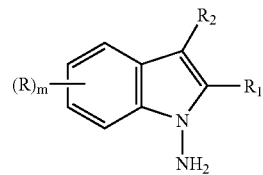

The process of this aspect of the invention comprises the following steps:

(a) In step (a), a solution of hydroxylamine-O-sulfonic acid (HOSA) is prepared in a suitable organic solvent.

(b) In step (b), a solution of a suitable base is prepared in a suitable organic solvent.

(c) In step (c), a solution of a compound of the formula I is prepared in a suitable organic solvent.

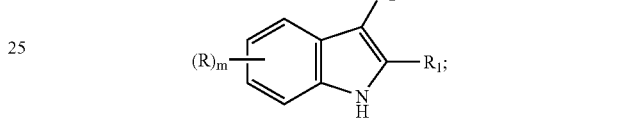

(d) Finally, in step (d), the solution prepared in step (a) and the solution prepared in step (b) are added simultaneously and proportionally to the solution prepared in step (c), which is taken in a suitable reaction vessel at a suitable reaction temperature to provide the compound of formula (II) in high purity and high yields.

Wherein:

R is hydrogen, $C_1$–$C_4$-alkyl, $C_1$–$C_4$-alkoxy, benzyloxy or fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and sum of x and y is 2n+1;

$R_1$ and $R_2$ are the same or different and are each independently selected from hydrogen, $C_1$–$C_4$-alkyl, $C_1$–$C_4$-alkoxy, benzyloxy or fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and sum of x and y is 2n+1; or $R_1$ and $R_2$ taken together with the carbon atoms to which they are attached form a $C_5$–$C_8$cyclic ring; and m is 1 or 2.

It is to be noted that the compound of formula (II) can be prepared using the steps as described hereinabove, not necessarily in different reaction vessels but may be in the same reaction vessel essentially using these steps. Also, the order in which the reactants are added can be altered if necessary by changing the order of steps.

In one aspect of the process of this invention, any suitable organic solvent known to one skilled in the art can be employed in steps (a) and (b) of the process of this invention. Specific types of organic solvents that may be employed include broadly polar aprotic solvents as well as a variety of non-polar aprotic solvents or mixtures thereof. As used herein, aprotic organic solvent means that it is neither a proton donor nor a proton acceptor. Generally, aprotic solvents are more suitable in steps (a) and (b) of the process of this invention.

Representative examples of aprotic solvents that are suitable in the process of this invention include, without any limitation, N-methylpyrrolidinone (NMP), N,N-dimethylformamide (DMF), dimethyl acetamide (DMAc), dimethyl sulfoxide (DMSO), hexamethyl phosphoramide (HMPA), and the like. Mixtures of these solvents in any proportions can also be employed. Examples of non-polar organic solvents include without limitation, tetrahydrofuran (THF), n-hexane, n-heptane, petroleum ether, and the like. Various halogenated solvents such as dichloromethane, chloroform, carbon tetrachloride, 1,2-dichloroethane, and the like can also be employed. Further combination of any polar and non-polar solvents, such as NMP/hexane, NMP/heptane, etc. can also be employed.

As noted, the process of this invention utilizes a base in the step (b) of the process of this invention. Generally, any base that can bring about the required action can be employed in this step of the process of this invention. It is generally advantageous to use an organic base in this step, especially an organic base which is soluble in the solvent employed. Thus, the reaction can be carried out in a homogeneous fashion. In addition, a base which is having a $pK_a$ value at least about the same as that of indole is more suitable in this step of the process of this invention.

Suitable organic base for this step include an alkaline metal alkoxide. Examples of suitable alkaline metal alkoxides, include without limitation, lithium methoxide, lithium ethoxide, lithium isopropoxide, lithium tert-butoxide, sodium methoxide, sodium ethoxide, sodium isopropoxide, sodium tert-butoxide, potassium methoxide, potassium ethoxide, potassium isopropoxide, potassium tert-butoxide, cesium methoxide, cesium ethoxide, cesium isopropoxide, cesium tert-butoxide, and the like. A mixture of organic bases can also be employed. It has been found that potassium tert-butoxide is particularly suitable alkaline metal alkoxide in the practice of the process of this invention.

In step (c) of the process of this invention, the solvent used is also an aprotic solvent. Any of the aprotic solvents listed above may be used in this step of the process of this invention. The same solvent as that used in steps (a) and (b) may be employed in this step as well. For instance, such aprotic solvents include, without limitation, NMP, DMF, DMAc, and the like, and/or mixtures thereof.

Any of the reaction temperature that will bring about the intended result can be employed in the process of this invention. Generally, suitable reaction temperature may be in the range of sub-ambient to ambient temperatures. For instance, the reaction temperature from about −5° C. to about 40° C. is suitable to carry out the process of this invention. Even more suitably, the reaction temperature from about 0° C. to about 25° C. may be employed in the process of this invention. It is generally understood and appreciated by one skilled in the art that higher temperature generally increase the rate of reaction. Thus, in certain instances superambient temperatures, that is, higher than room temperatures up to reflux temperature of the solvent may be employed.

In general, the process of this invention is carried out with an excess amount of the base. For instance, the base may be present in an amount of from about 1 mole to about 10 moles with reference to the compound of formula I. However, the base may be present in an amount of from about 3 mole to about 6 moles with reference to the compound of formula I in order to carry out the process of this invention.

Similarly, HOSA is present in excess amounts when compared with the compound of formula (I). It is generally advantageous to use more than a molar excess of HOSA in the process of this invention. More advantageously, it has now been found that only about two molar excess of HOSA is sufficient to bring about optimum results by the practice of this invention.

The contacting of the reaction solutions prepared in steps (a) and (b) with the reactant solution from step (c) can be carried out by any of the known methods in the art. For instance, without limitation, such contacting in step (d) may be performed in a continuous reactor wherein the reactants are continuously fed, or by means of static mixing, e.g. static mixing with a limited residence time or static mixing combined with a loop system, or by means of a microreactor. For this purpose, various known static mixers, continuous reactors and microreactors can be employed. Continuous reactions may be worked-up in a continuous manner or batch-wise by methods known in the art.

The contacting in step (d) can also be affected in a batch reactor. Any of the known reactors that will bring about the desired result can be employed. For instance, in a batch operation, the reaction solutions from steps (a) and (b) are fed into a reactor such as stirred tank reactor, which contained the reaction solution from step (c). Various modifications known to one skilled in the art can be used in affecting these additions of reaction solutions in this mode of the operation.

As mentioned hereinabove, various nitrogen heterocyclic compounds can be employed in the process of this invention. For instance, without any limitation, a compound of the formula (I) wherein R and $R_1$ are hydrogen and $R_2$ is methyl can be used in the process of this invention. A compound of formula (I) wherein $R_1$ and $R_2$ taken together with the carbon atoms to which they are attached form a benzene ring is also preferred. Specific examples of such compounds are as described hereinabove. For instance, substituted or unsubstituted carbazole can be employed.

In another aspect of this invention there is also provided another process for the preparation of a compound of the formula II as described herein. The process of this aspect of the invention comprises the following steps. In step (a), a solution of hydroxylamine-O-sulfonic acid and a compound of the formula I as described herein is prepared in a suitable organic solvent. In step (b), a solution of a suitable base is prepared in a suitable organic solvent. In step (c), the solution prepared in step (a) is contacted simultaneously and proportionally with the solution prepared in step (b) at a suitable reaction temperature to provide the compound of formula (II) in high purity and high yields. Wherein R, $R_1$, $R_2$, and m are as defined above.

Again, the above process of the invention can be carried out using any of the reactors known in the art. For instance, without any limitation, a stirred tank reactor, a continuous reactor, a microreactor, or a static mixer can be employed. The above process of the invention is particularly suitable for carrying out the amination reaction in a continuous stirred tank reactor.

In this embodiment of the invention, any of the solvents that are suitable to carry out this reaction can be employed. More suitably, all of the solvents as described hereinabove can also be employed in this embodiment. Generally, aprotic solvents such as NMP, DMF, or DMAc as described herein are more suitable solvents.

In this embodiment, the base used is the one which will bring about the intended result. Any of the known bases can be employed. However, more suitably, the base such as an organic base as described above can be used in this embodiment of the invention. Generally, it is more suitable to use an organic base which is soluble in the reaction solvent employed as described hereinabove. Specific examples of organic bases that are suitable in this embodiment include alkali metal alkoxide such as potassium tert-butoxide.

It is also appreciated by one skilled in the art that any of the reaction temperature that will bring about the intended result can be employed in this embodiment of the process of this invention. To reiterate, as described hereinabove, generally subambient to ambient temperatures are suitable to carry out this process of this invention. However, in certain situations superambient temperatures may also be employed.

Furthermore, it is generally advantageous to carry out this process of the invention with excess amounts of base as well as HOSA when compared with the compound of formula (I). More advantageously, as noted above, even in this embodiment, only about two molar excess of HOSA is sufficient to bring about optimum results. Similarly, from about 1 mole to about 10 moles excess of base may be employed, but base may be present in an amount of from about 3 mole to about 6 moles with reference to the compound of formula I as noted hereinabove.

In yet another aspect of this invention there is also provided a process for the preparation of a compound of the formula IV:

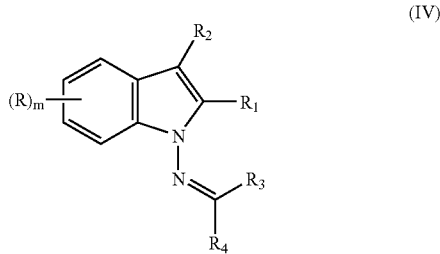

In this aspect of the invention, the process involves the following. A solution of hydroxylamine-O-sulfonic acid in a suitable organic solvent and a solution of a suitable base in a suitable organic solvent are added simultaneously and proportionally to a solution of a compound of the formula I, as described herein, in a suitable organic solvent at a suitable reaction temperature wherein the compound of the formula (I), as described herein, is taken in a suitable reaction vessel, as described above. This reaction provides a compound of the formula (II) as described herein.

The resulting N-amino-indole compound (II) is then reacted in the same reaction vessel with a compound of the formula (III):

to provide a compound of the formula (IV). Wherein R, $R_1$, $R_2$, and m are as defined above, and $R_3$ and $R_4$ are the same or different and are each independently selected from hydrogen or $C_1$–$C_4$-alkyl.

In this embodiment of this invention, the amination of the compound of the formula (I) to compound of the formula (II) is carried out using essentially similar procedures as described above in the other two embodiments of this invention. Thus, all of the solvents, bases and reaction vessels described above can be used in this embodiment. Similarly, same reaction conditions as described above can be employed. In general, an aprotic solvent such as NMP, DMF or DMAc and an organic base such as potassium tert-butoxide with HOSA at temperatures in the range of from about –5° C. to about 40° C. can be employed. The temperature in the range of from about 0° C. to about 25° C. is particularly preferred.

Furthermore, as noted above, it is generally advantageous to carry out this process of the invention with excess amounts of base as well as HOSA when compared with the compound of formula (I). More advantageously, as noted above, even in this embodiment, only about two molar excess of HOSA is sufficient to bring about optimum results. Similarly, from about 1 mole to about 10 moles excess of base may be employed, but base may be present in an amount of from about 3 mole to about 6 moles with reference to the compound of formula I as noted hereinabove.

Advantageously, it has now been found that the reaction of the compound of formula (II) with a compound of formula (III) can be carried out in the same reaction vessel by the addition of compound of formula (III). Generally, the compound of formula (III) can be added alone after the formation of compound of formula (II). However, it may be advantageous to add some organic or inorganic acids. Suitable organic acids include acetic acid, propanoic acid, n-butyric acid, and the like. It has also been found that use of water with organic acid is beneficial. Suitable inorganic acids include hydrochloric acid, nitric acid, sulfuric acid, and the like. Generally, the acid is added to an amount such that the reaction medium is maintained at a pH of about 4.

This addition reaction can generally be carried out at ambient temperatures, but subambient to superambient temperatures can also be employed depending upon the type of the compounds of formulae (II) and (III) are employed. Generally, temperatures in the range of from about 0° C. to about 100° C. can be employed. Temperatures in the range of from about 5° C. to about 30° C. are preferred. More particularly ambient temperature around 20° C. is preferred.

Various compounds of formula (III) can be employed in this process of the invention. Examples of such compounds include without limitation, various known aldehydes and ketones. Specific examples of aldehydes include, without any limitation, formaldehyde, acetaldehyde, propionaldehyde, n-butyraldehyde, iso-butyraldehyde, benzaldehyde, phenylacetaldehyde, and the like. Suitable ketones for this process include without any limitation, acetone, methyl ethyl ketone, diethyl ketone, acetophenone, benzophenone, and the like. In general, aldehydes are more suitable reactants in this process of the invention, propionaldehyde being most suitable compound of formula (III).

In a further aspect of this invention, an embodiment of this invention includes a product produced in accordance with this process of the invention. Specifically, the product produced in accordance with this process of this invention is having R, $R_1$, and $R_4$ are hydrogen, $R_2$ is methyl and $R_3$ is ethyl. More specifically, the product produced in accordance with this process of the invention is 3-methyl-N-(propylidene)-1H-indol-1-amine.

Finally, in yet another aspect of this invention there is also provided a process for the preparation of a compound of the formula VI:

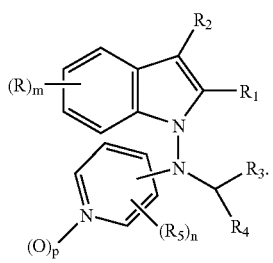

(VI)

In this aspect of the invention, the process involves the following steps:

In step (a) of this process embodiment of the invention, the compound of formula (IV) as described herein is first prepared essentially following the procedures of the above mentioned embodiment. That is, a solution of hydroxylamine-O-sulfonic acid in a suitable organic solvent and a solution of a suitable base in a suitable organic solvent are added simultaneously and proportionally to a solution of a compound of the formula I in a suitable organic solvent at a suitable reaction temperature wherein the compound of the formula (I), as described herein, is taken in a suitable reaction vessel. This reaction provides a compound of the formula (II) as described herein.

The resulting N-amino-indole compound (II) is then reacted in the same reaction vessel with a compound of the formula (III) to provide a compound of formula (IV).

In step (b) of this process of the invention, the compound of formula (IV) is reacted with a suitable reducing agent to provide a compound of formula (V):

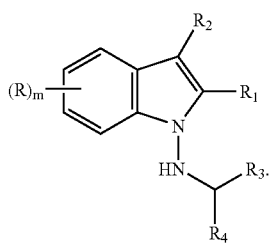

(V)

Finally, in step (c) of this process of the invention, the compound of formula (V) is then reacted with a compound of the formula (VII):

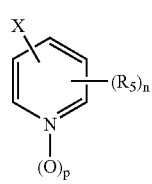

(VII)

in the presence of a suitable base in a suitable organic solvent to provide the compound of formula (VI). The compound of the formula (VI) is optionally treated with an inorganic acid such as hydrochloric acid to provide a salt (such as hydrochloride) of the compound of the formula (VI). Wherein R, $R_1$, $R_2$, $R_3$, $R_4$ and m are as described above. $R_5$ is hydrogen, nitro, amino, halogen, $C_{1-4}$-alkyl, $C_{1-4}$-alkanoylamino, phenyl-$C_{1-4}$-alkanoylamino, phenylcarbonylamino, alkylamino or phenyl-$C_{1-4}$-alkylamino; X is halogen; n is 1 or 2 and p is 0 or 1.

Again, it is to be understood that the steps discussed hereinabove are for illustrative purposes only. The order in which these steps are carried out may be altered and/or one ore more of these steps can be carried out simultaneously and/or concurrently. Thus, various modifications of these steps also form part of this invention. More advantageously, all of these steps can be carried out in the same reaction vessel in a single batch operation or in a continuous reactor.

Thus in accordance with this aspect of the invention, in step (a) of this embodiment, the amination of the compound of formula (I) to form the compound of formula (II) is carried out essentially in the same manner as described above by employing a solvent, preferably an aprotic solvent, a base, preferably an organic base, and HOSA at around subambient to ambient reaction temperatures.

The compound of the formula (II) so formed is then converted to compound of the formula (IV), generally in the same reaction vessel, by reacting it with the compound of formula (III) as described above. The reaction conditions and the suitable compounds of the formula (III) are the same as the one described above.

As noted, the compound of the formula (IV) is then reduced to compound of formula (V). This reduction reaction can be carried out using any of the known procedures in the art. In general, the reduction can be carried out using any of the known C=N reducing agents such as the one used typically for reducing a Schiff base, hydrazone or an imine. Examples of suitable reducing agents include, without limitation, lithium aluminum hydride, sodium borohydride, sodium borohydride and glacial acetic acid, sodium acetoxyborohydride, sodium diacetoxyborohydride, sodium triacetoxyborohydride, sodium cyanoborohydride, sodium-ethanol, hydrogen and a catalyst, and the like.

Other reducing agents such as dibutyl tin hydrochloride ($Bu_2SnClH$) in HMPA can also be employed. Various boron reagents can also be employed. Specific examples include, diborane, boron-sulfide complex such as boron-dimethyl sulfide or boron-1,4-thioxane complex; a boron etherate such as boron-THF complex; a boron-amine complex such as boron-ammonia, boron-tert-butylamine, boron-N-ethyl-diisopropylamine, boron-N-ethylmorpholine, boron-N-methylmorpholine, boron-morpholine, boron-piperidine, boron-pyridine, boron-triethylamine, and boron-trimethylamine; a boron-phosphine complex such as boron-tributylphosphine or boron-triphenylphosphine; a mixture of borohydrides such as sodium borohydride and tetra-alkylammonium borohydride; a reagent which generates in situ borane, for example, a combination of sodium borohydride and iodine, sodium borohydride and $BF_3$-dietherate, sodium borohydride and chlorotrimethylsilane, tetra-alkylammonium borohydride and an alkyl bromide such as n-butylbromide; etc. It has now been found that sodium borohydride in the presence of glacial acetic acid is generally a more suitable reducing agent in this step of the process of the invention.

The reduction reaction is also carried out in the presence of a suitable organic solvent. Typically an aprotic polar solvent such as the one described herein is more suitable to carry out the reduction step. Specific examples of such organic solvents include, without limitation, NMP, DMF, DMAc, THF, heptane, hexane, toluene, petroleum ether, and the like.

Surprisingly, it has now been found that a mixture of a polar aprotic solvent and a non-polar solvent particularly provides several advantages in carrying out this reduction step. Specific examples of such mixtures of solvents include without limitation, NMP/heptane, NMP/hexane, NMP/petroleum ether, DMF/hexane, DMF/n-heptane, and the like. Particularly, it has now been found that a mixture of NMP and n-heptane provides certain advantages in this process of the invention in that it reduces considerably the foaming of the reagents.

The reduction of compound of the formula (IV) to compound of the formula (V) can generally be carried out at any temperature that would bring about the desired result. Thus, subambient to ambient to superambient temperatures can be employed depending upon the type of compounds and reagents employed. In general, temperature in the range of from about 0° C. to about 60° C. is suitable. Temperatures in the range of from about 5° C. to 40° C. are typically employed. A temperature of about 30° C. is preferred.

The compound of formula (V) can further be isolated as a suitable salt such as hydrochloride by reacting with suitable acid such as hydrochloric acid. In general, the salts of compounds of formula (V) are crystalline solids and thus provide a method to purify compounds of the formula (V) if needed before converting it to the compound of the formula (VI) in a subsequent reaction with the compound of the formula (VII).

The reaction of the compound of the formula (V) can be carried out with a variety of pyridine derivatives of the formula (VII) to form the compound of the formula (VI), preferably with a compound of the formula (VII) wherein X is Cl and p is 0. Examples of such compounds of the formula (VII) include without limitation, 4–Chloropyridine, 4-chloro-3-fluoro-pyridine, 4-chloro-2-fluoro-pyridine and 4-chloro-3,5-difluoro-pyridine.

The reaction is carried out in an aprotic polar solvent as used in the previous process step such as, without limitation, NMP, DMF, DMAc, THF, heptane, hexane, toluene, petroleum ether, and the like, or in a mixture of a polar aprotic solvent and a non-polar solvent such as without limitation, NMP/heptane, NMP/hexane, NMP/petroleum ether, DMF/hexane, DMF/n-heptane, and the like. Various other solvents can also be employed in this step of the process of this invention. Examples of solvents that are suitable in this step include ethereal solvents such as bis(2-methoxyethyl)ether, diethyl ether, dimethoxy ether, dioxane or THF; polar aprotic solvents as described herein which include DMF, DMAc, HMPA or DMSO; or protic solvents such as methanol, ethanol, isopropanol, and the like. Also, as noted, any combination of mixtures of these solvents can also be employed. Typically, this reaction is carried out using the same solvent such as NMP or a mixture of NMP and heptane.

A suitable organic base for this step includes an alkaline metal alkoxide. Examples of suitable alkaline metal alkoxides, include without limitation, lithium methoxide, lithium ethoxide, lithium isopropoxide, lithium tert-butoxide, sodium methoxide, sodium ethoxide, sodium isopropoxide, sodium tert-butoxide, potassium methoxide, potassium ethoxide, potassium isopropoxide, potassium tert-butoxide, cesium methoxide, cesium ethoxide, cesium isopropoxide, cesium tert-butoxide, and the like; alkali metal hydrides such as sodium hydride or potassium hydride and the like. A mixture of organic bases can also be employed. It has been found that potassium tert-butoxide is particularly suitable alkaline metal alkoxide in the practice of this step of the process of this invention.

The reaction of compound of the formula (V) with a pyridine derivative (VII) to form compound of the formula (VI) can generally be carried out at any temperature that would bring about the desired result. Thus, subambient to ambient to superambient temperatures can be employed depending upon the type of compounds and reagents employed. In general, temperature in the range of from about 70° C. to about 150° C. is suitable.

The compound of the formula (VI) can further be reacted with suitable inorganic acid to yield a suitable salt of the compound of the formula (VI). An example of such an inorganic acid is hydrochloric acid, resulting in the hydrochloride of the compound of the formula (VI). In general, the salts of compounds of the formula (VI) are crystalline solids and thus provide a method to purify compounds of the formula (VI) if needed before employing it for example pharmaceutical purposes.

The reaction can be carried out in the same reaction vessel or in a different vessel after isolation of the compound of the formula (V) as noted above. The above process of the invention can be carried out using any of the reactors known in the art. Again, a stirred tank reactor, a continuous reactor, a microreactor or a static mixer may be used. The above process of the invention is particularly suitable for carrying out the coupling reaction in a static mixer with a loop system or a continuous stirred tank reactor. Advantageously, the reaction is worked-up in a batch-wise manner.

In a further aspect of this invention, an embodiment of this invention includes a product produced in accordance with this process of the invention. Specifically, the product produced is N-(n-propyl)-N-(3-fluoro-4-pyridinyl)-1H-3-methylindol-1-amine hydrochloride.

Yet in another aspect of this invention there is also provided a compound of the formula (IV), wherein said substituents are as described herein with the proviso that when R and $R_3$ are hydrogen, $R_4$ is not hydrogen or methyl.

As noted, a few of the compounds within the scope of the formula (IV) are known and therefore have been excluded from this invention. For instance, Somei, et al. Tet. Lett. No. 41, pp 3605–3608 (1974), which is incorporated herein by reference in its entirety, describe compounds of the formula (IV) wherein m=0, R, $R_1$, $R_3$=H, $R_2$=methyl, $R_4$=methyl.

In a further aspect of this embodiment of the invention, a suitable compound of the formula (IV) is one in which R, $R_1$ and $R_3$ are hydrogen and $R_2$ is methyl. Specific compounds within the scope of this invention include without any limitation the following:

3-methyl-N-(propylidene)-1H-indol-1-amine;
N-(propylidene)-1H-indol-1-amine;
5-benzyloxy-N-(propylidene)-1H-indol-1-amine;
5-methoxy-N-(propylidene)-1H-indol-1-amine; and
N-(propylidene)-1H-carbazol-1-amine.

This invention is further illustrated by the following examples which are provided for illustration purposes and in no way limit the scope of the present invention.

EXAMPLES (GENERAL)

In the Examples that follow, the following abbreviations are used:
HOSA Hydroxylamine-O-sulfonic Acid
HPLC High Performance Liquid Chromatography
KOtBu Potassium tert-butoxide
NMP N-methylpyrrolidinone
NMR Nuclear Magnetic Resonance Spectroscopy General Analytical Techniques Used for the Characterization: A variety of analytical techniques were used to characterize compounds prepared in accordance with the practice of this invention, which included the following:

$^1$H, $^{13}$C and $^{19}$F NMR spectra were recorded using a Varian XL300 or a Gemini 300 spectrophotometer operating at 300, 75, and 282 MHz, respectively. The $^1$H NMR spectral data is presented as δ in parts per million (ppm) with reference to tetramethylsilane (TMS) as the internal standard and following abbreviations are used in summarizing the data: s=singlet, d=doublet; t=triplet; q=quartet; m=multiplet; dd=doublet of doublets; br=broad. HPLC data were collected on a Perkin-Elmer Integral 4000 liquid chromatograph typically using a 3.9×150 mm, Waters Symmetry $C_{18}$ column, 5 μg, isocratic mobile phase of acetonitrile/0.1 N ammonium formate, flow of 1.0 mL/min, and UV detection. Mass spectra were obtained on a Finnigan TSQ 700 spectrometer. Elemental analyses were performed by Robertson Microlit, Inc. Further abbreviations used herein include the following: LC=liquid chromatograph; MS=mass spectrograph; EI/MS=electrospray impact/mass spectrograph; RT=retention time; M+=molecular ion.

Example 1

1H-indol-1-amine

A solution of 33.8 kg (32.8 kg corrected for 97% purity) of hydroxylamine-O-sulfonic acid (HOSA) and 15.8 kg (15.6 kg corrected for 99% purity) of indole in 120.2 kg of N-methylpyrrolidinone (NMP), is prepared and chilled to 0–5° C. A second solution is prepared from 67.0 kg (63.7 kg corrected for 95% purity) of potassium tert-butoxide and 122.6 kg of NMP. An amination vessel is charged with 47.0 kg of NMP and an initial charge of 2.2 kg of the potassium tert-butoxide/NMP solution. The HOSA/indole/NMP solution and the remaining potassium tert-butoxide/NMP solution are then simultaneously and proportionally metered using a metering pumping system consisting of a dual head plunger pump together with coriolis mass flow meters into the amination vessel over a period of 185 minutes while maintaining a reaction temperature of 20–30° C. to yield a solution containing 15.9 kg (90.2% yield) of 1H-indol-1-amine as determined by external standard HPLC assay.

Example 2

5-Benzyloxy-1H-indol-1-amine

A solution of 5.3 kg (5.2 kg corrected for 97% purity) of hydroxylamine-O-sulfonic acid (HOSA) in 19.1 kg of N-methylpyrrolidinone (NMP), is prepared and chilled to 0–5° C. A second solution is prepared from 10.6 kg (10.0 kg corrected for 95% purity) of potassium tert-butoxide and 19.3 kg of NMP. An amination vessel is charged with 5.0 kg (4.7 kg corrected for 94% purity) of 5-benzyloxyindole, 15.5 kg of NMP and an initial charge of 0.4 kg of the potassium tert-butoxide/NMP solution. The HOSA/NMP solution and the remaining potassium tert-butoxide/NMP solution are then simultaneously and proportionally metered into the amination vessel over a period of 166 minutes while maintaining a reaction temperature of 14–29° C. to yield a solution containing 4.3 kg (86.0% yield) of 5-benzyloxy-1H-indol-1-amine as determined by external standard HPLC assay. After adding 105 L water, and cooling to 0–5° C., the mixture is filtered. The filtered solid is partitioned with 63 L n-butyl acetate and 8.5 L water, then filtered. The organic phase is concentrated under reduced pressure to give a solid which contains 3.9 kg (77.4% yield) of 5-benzyloxy-1H-indol-1-amine as determined by external standard HPLC assay.

Example 3

5-Methoxy-1H-indol-1-amine

A solution of 10.0 g (9.7 g corrected for 97% purity) of hydroxylamine-O-sulfonic acid (HOSA) in 33.7 g of N-methylpyrrolidinone (NMP) is prepared and chilled to 0–5° C. A second solution is prepared from 20.1 g (19.1 g corrected for 95% purity) of potassium tert-butoxide and 34.4 g of NMP. An amination vessel is charged with 5.9 g of 5-methoxyindole, 17.8 g of NMP and an initial charge of 0.7 g of the potassium tert-butoxide/NMP solution. The HOSA/NMP solution and the remaining potassium tert-butoxide/NMP solution are then simultaneously and proportionally metered into the amination vessel over a period of 86 minutes while maintaining a reaction temperature of 15–22° C. to yield a solution containing 5.6 g (87% yield) of 5-methoxy-1H-indol-1-amine as determined by internal standard HPLC assay.

Example 4

1H-Carbazol-1-amine

A solution of 10.0 g (9.7 g corrected for 97% purity) of hydroxylamine-O-sulfonic acid (HOSA) in 35.9 g of N-methylpyrrolidinone (NMP) is prepared and chilled to 0–5° C. A second solution is prepared from 20.3 g (19.3 g corrected for 95% purity) of potassium tert-butoxide and 35.3 g of NMP. An amination vessel is charged with 7.0 g (6.7 g corrected for 99% purity) of carbazole, 21.7 g of NMP and an initial charge of 1.3 g of the potassium tert-butoxide/NMP solution. The HOSA/NMP solution and the remaining potassium tert-butoxide/NMP solution are then simultaneously and proportionally metered into the amination vessel over a period of 86 minutes while maintaining a reaction temperature of 22–30° C. to yield a solution containing an 85% yield of 1H-carbazol-1-amine as determined by HPLC.

Example 5

1H-3-methyl-indol-1-amine

A 36.1% (wt/wt) solution of KOtBu/NMP (enough for 2 amination batches) is prepared by charging a 30-gal Hastelloy reactor under nitrogen with 35.6 kg of potassium tert-butoxide and 63.1 kg of N-methylpyrrolidinone (NMP), and then stirring at 20–25° C. for 30 min. A 19.0% (wt/wt) solution of hydroxylamine-O-sulfonic acid (HOSA) in NMP (enough for 2 amination batches) is prepared by charging a 30-gal Hastelloy reactor under nitrogen with 75.4 kg of NMP and a total of 17.7 kg of HOSA (in three portions over a period of 45 min), stirring at 30–35° C. for 40 min (until dissolution occurred), then cooling to 10° C. An amination vessel is prepared by charging a 30-gal glass-lined reactor under nitrogen with 4.5 kg (34.3 mole) of 3-methylindole, 10.0 L of NMP and 0.4 kg (0.1 equiv.) of potassium tert-butoxide. A proportional pumping system consisting of a dual-head plunger pump and a pair of mass flow meters is used to simultaneously pump the HOSA solution at 0.47 kg/min and pump the KOtBu solution at 0.49 kg/min to the amination reactor (through subsurface sparging tubes in the amination vessel). The temperature of the slightly exothermic amination process was controlled at 25–35° C. by adjusting jacket cooling. The feeds are stopped after 90 min, at which time a total of 43.9 kg of the KOtBu solution (4.1 equiv.) and 42.0 kg of the HOSA solution (2.1 equiv.) had been charged, and a 97% conversion to N-amino-3-methylindole is achieved (by HPLC assay). The work up is performed in two portions. Half of the batch is transferred to a quench vessel (30-gal reactor) that contained 60 L of cold water and 12 L of toluene. After stirring for 10 min at 20–25° C., the phases are separated. The aqueous phase is extracted with 3×12-L portions of toluene. The other half of the batch is worked up similarly. The organic phases from each portion of the work up are combined and concentrated (60° C., <50 mbar, 50-L rotary evaporator) to give 5.2 kg of N-amino-3-methylindole as a pasty solid, corresponding to 4.5 kg of product corrected for solvent as determined by NMR (3.4 wt % toluene and 6.9 wt % NMP), 89.7% yield, 95.9% pure by HPLC assay.

Similarly, a second amination is performed following the same procedure described above using the remaining portions of the HOSA and KOtBu solutions, to obtain 4.6 kg (corrected) of N-amino-3-methylindole, 91.1% yield.

Example 6

1H-indol-1-amine

Step 1 —Preparation of HOSA/indole solution: A 50-gal glass lined steel reactor is charged with 120.2 kg (116.3 L) NMP under nitrogen purge and slight exhaust, while the reactor temperature is maintained at 19–23° C. With agitation (ca. 130 rpm), charge 33.8 kg (32.8 kg corrected for 97% purity) HOSA in three portions (ca. 15.8 kg, 9.0 kg and 9.0 kg) through the manhole ca. 15–30 min apart. Expect an initial exotherm of 10–15° C. temperature rise. Circulate chilled water through the jacket or use gentle jacket heating to maintain a pot temperature of 20–35° C. (preferably 30–35° C. to facilitate dissolution). Expect dissolution after 1–2 h agitation. Cool the contents of the reactor to a temperature of about 20° C. (10–25° C.) and charge 15.8 kg (15.6 kg corrected for 99% purity) indole through the manhole. After dissolution (several minutes), cool the contents of the reactor to a temperature of about 0–5° C. (–5 to 15° C.), reduce agitation to about 50 rpm and then maintain a temperature at around 0–5° C. (–5 to 15° C.) for the remainder of the process.

Step 2—Preparation of the potassium tert-butoxide solution: A 50-gal glass-lined steel reactor equipped with an empty condenser line is charged with 122.6 kg (118.7) NMP under nitrogen purge and slight exhaust, while maintaining the reactor temperature around 17–19° C. (15–22° C.). Charge 67.0 kg (63.7 kg corrected for 95% purity) potassium tert-butoxide (KOtBu) through the manhole at agitation ca. 150 rpm (100–200 rpm). Observe slight exotherm to 20–25° C. Cool if necessary to keep temperature below 25° C. After dissolution is attained (within 15–60 min), stir at about 50 rpm and at a temperature of about 17–25° C. for the remainder of the process.

Step 3—Amination: A 150-gal glass-lined steel reactor is charged with 47.0 kg (45.5 L) NMP under nitrogen purge and slight exhaust, and cool to 10–22° C. with agitation at about 180 rpm. Charge an initial amount of about 0.05 equiv of KOtBu solution from step 2 (6.7 mole, total 2.2 kg of the solution). Then simultaneously pump the two solutions prepared above in steps 1 and 2 at the following rates: HOSA/indole solution from step 1 at a rate of 0.8 L/min=0.9 kg/min for 187.4 min total time; and KOtBu solution from step 2 at a rate of 1.0 L/min=1.0 kg/min for 187.4 min total time through sparging tubes (⅜-in o.d. 304 SS tubing) inserted in nozzles at opposite sides of the reactor head (about 180 degrees apart) while maintaining good agitation (>180 rpm) and maintaining the reaction temperature at about 15–30° C., preferably 24–30° C., using chilled water cooling. Monitor the progress of the reaction by withdrawing samples of the reaction mixture for HPLC assay, as further detailed below, at 0.5 equiv. intervals of HOSA charged (every 43 min, 35 sec during the simultaneous reagent feeds). Continue the simultaneous proportional feed until all of the reagents (133.5 mole scale) have been charged and the amination is judged complete as evidenced by HPLC assay. Rinse both of the reactors from steps 1 and 2 with L NMP each and pump the rinse to the 150-gal reactor in this step. The batch from this step is then used, as is, for the next step in the preparation of N-propylidene-1H-indol-1-amine.

The reaction mixture is monitored by a HPLC assay using the following conditions:
Column: Phenomenex, IB-SIL 5 Phenyl, 150×4.6 mm, 5 micron
Mobile Phase: 65:35 0.1 N ammonium formate/acetonitrile
Flow: 1.5 mL/min
Detection: UV at 275 nm
Sample Prep: dilute ca. 15 µL of reaction mixture with 2 mL 50:50 mixture of the mobile phase
Injection: 10 µL Example 7

N-propylidene-1H-indol-1-amine

To the 1H-indol-1-amine solution prepared in accordance with the procedures set forth in Example 6 in a 150-gal steel reactor, under nitrogen purge, slight exhaust, agitation ca. 150 rpm, at 10–25° C. (preferably 10–18° C.) and with slow jacket cooling, charge approximately 21.6 kg acetic acid to pH 3.9–4.0 (0.1 mL of the reaction mixture in 5 mL water) at a rate of ca. 1 kg/min. Charge incrementally more HOAc if needed to attain the pH level. Rinse pump with ca. 2 L NMP. Charge 10.8 L water (a slight temperature rise of about 3–6° C. is expected), essentially in one portion (ca. 1 min addition time). Charge 14.4 kg (13.9 kg corrected for 97% purity) propionaldehyde at ca. 0.8 kg/min (0.5–1.0 kg/min) while maintaining 10–24° C., preferably 10–20° C. A mild exotherm is expected. Depending on the rate of addition and cooling, expect about a 5° C. temperature rise. Rinse pump with ca. 3 L NMP. Agitate at 10–24° C., preferably 17–20° C., until the reaction is judged complete as evidenced by the HPLC assay, conditions of which are detailed further below (>99% conversion in 2–3 h). Monitor the progress of the reaction by withdrawing samples of the reaction mixture for HPLC assays. When the reaction is judged complete, prepare for a vacuum distillation directly from the reactor to a suitable receiver. Expect a forerun (ca. 45–50 L) of volatiles including tert-butanol and water initially at 50–70° C. and ca. 30–40 mm pressure. As the distillation rate slows, gradually increase the pot temperature to 95–100° C. and reduce the pressure to 5–25 mm and begin collecting NMP. Collect a total of about 320 kg distillates (to give a pot weight of 9.5 parts w/w with respect to the initial indole charge), then release the vacuum with nitrogen and cool to 10–25° C. If necessary, or for convenience of scheduling, the distillation can be interrupted at any time, by releasing the vacuum with nitrogen, cooling to <30° C., storing under nitrogen, and then restarting as required. Work up the reaction by charging 133 L heptane followed by, with chilled water cooling to keep exotherm temperature below 30° C., 234 L water through a reactor charging nozzle (maximum process volume of ca. 450 L is attained). Agitate for >10 min, then separate the phases. Extract the bottom aqueous phase with 54 L heptane. Combine the organic extracts, and wash with aqueous potassium bicarbonate solution (prepared from 0.6 kg potassium bicarbonate dissolved in 58 L (58–95 L) water) followed by a 58 L water wash. Concentrate the organic phase to obtain crude N-propylidene-1H-indol-1-amine as an oil. Purify by short path distillation, first pass to remove volatiles at ca. 120° C. evaporator and ca. 200–800 mbar pressure, and then a second pass at 110° C. evaporator and 0.2–0.4 mbar pressure to collect purified product.

The reaction mixture is monitored by a HPLC assay using the following conditions:

Column: Phenomenex, IB-SIL 5 Phenyl, 150×4.6 mm, 5 micron

Mobile Phase: 65:35 0.1 N ammonium formate/acetonitrile

Flow: 1.5 mL/min

Detection: UV at 275 nm

Sample Prep: add 2 drops of the reaction mixture per 1 mL of acetonitrile, inject 10 µL Example 8

N-(Propylidene)-1H-indol-1-amine

A solution of 86.6 g (771 mmol) of potassium tert-butoxide is prepared in 160 mL N-methylpyrrolidone (NMP). Also prepared is a solution of 36.4 g (322 mmol) of hydroxylamine-O-sulfonic acid (HOSA) in 175 mL NMP. Cool the HOSA-solution after a clear solution is obtained to 10° C.

Additionally prepare a solution of 11.9 g (102 mmol) indole in 20 mL NMP, add an initial amount of 0.08–0.12 eq. KOtBu-solution to the indole solution. The HOSA and the KOtBu-solution are then added over a period of 60 min simultaneously and proportionally via a dual syringe pump at 20° C. to the reaction mixture. After completion of this addition, add 9 mL (500 mmol) water, 12 mL (300 mmol) glacial acetic acid and 15 mL (173 mmol) propionaldehyde to the resulting dark brown suspension. Stir the mixture at 20° C. until completion of the reaction. The reaction mixture is then worked-up by adding 500 mL water and 200 mL n-heptane. The phases are separated. The water phase is again extracted one time with 300 mL n-heptane and again twice with 200 mL toluene. The combined organic phases are washed twice with 100 mL water. The resulting brown heptane-solution is evaporated to dryness. This results in 14 g N-(propylidene)-1H-indol-1-amine (80%) as a brown liquid.

bp. 130–135° C. (1.3–1.4 mbar) $^1$H-NMR (DMSO-d$_6$, 300 MHz, TMS) [δ, ppm]: 1.2 (t, 3H, CH$_3$), 2.5 (m, 2H, CH$_2$), (d, 1H, arom.), 7.1 (t, 1H, arom.), 7.2 (t, 1H, arom.), 7.6 (dd, 2H, arom.), 8.0 (d, 1H, arom.), 8.2 (t, 1H, NCH) MS (EI+, 70 eV): 172 [M$^+$], 116 [M$^+$–NC$_3$H$_6$]

Example 9

N-Propyl-1H-indol-1-amine

Prepare a solution of 12.3 g (69.7 mmol) N-(propylidene)-1H-indol-1-amine in 45 mL NMP, and add 1.6 g (41.8 mol) sodium borohydride. Then prepare a solution of 2.5 g (41.8 mmol) glacial acetic acid in 15 mL NMP. Add the acetic acid solution in about 30 min at 30° C. to the above reaction mixture. Immediately hydrogen evolution will occur. Stir the reaction mixture at 35° C. until completion of the reaction. At the completion of the reaction, the reaction mixture is worked-up by slowly adding 50 mL water at 35° C. Attention is taken during the addition of water so as to minimize foaming that occurs and by allowing enough head space for foaming. The free head space is kept as much as three times the volume of the liquid contents of the reactor so as to control the foaming. Extract the reaction mixture with 50 mL n-heptane, separate the phases and extract the water phase again with 25 mL n-heptane. Evaporate the combined organic phases to dryness. This results in 10.9 g N-propyl-1H-indol-1-amine (90%) as a brown liquid.

bp. 115–125° C. (1.1 mbar)

$^1$H-NMR (DMSO-d$_6$, 300 MHz, TMS) [δ, ppm]: 0.9 (t, 3H, CH$_3$), 1.35 (m, 2H, CH$_2$(m, 2H, NCH$_2$), 6.35 (d, 1H, arom.), 6.5 (t, 1H, NH), 7.0 (t, 1H, arom.), 7.15 (t, 1H, arom.), 7.4 (m, 1H, arom.), 7.5 (dd, 2H, arom.) MS (EI+, 70 eV): 174 [M$^+$+H], 131 [M$^+$+H–NHC$_3$H$_7$]

Example 10

(3-Fluoropyridin-4-yl)-(indol-1-yl)-propylamine hydrochloride

Prepare a solution of 18.0 g potassium tert-butoxide in 53 mL NMP and stir the suspension at 20° C. until a clear solution is obtained. Cool the solution to −20° C. Add to the cooled solution a mixture of 9.3 g (53.4 mmol) N-propyl-1H-indol-1-amine, 7.4 g (53.4 mmol) 4-chloro-3-fluoropyridine and 53 mL NMP while maintaining the internal reaction temperature around −15° C. After the addition is over, the reaction mixture is stirred for ~30 min at −20° C. The reaction mixture is then added to 100 mL water and 13 mL HCl (37%). Then, add 50 mL n-heptane (2×) and separate the phases. Add to the water phase 10 mL NaOH (32%) and extract the water phase twice with 50 mL n-butyl acetate, wash the combined n-butyl acetate phase with 50 mL water. Add to the resulting n-butyl acetate phase 4.5 mL HCl (37%). Distill the mixture using Dean-Stark trap to remove completely the water. During the distillation a solid precipitates. The suspension is cooled to 5° C. and filtered. After drying at 60–70° C., there remains 10.8 g (3-fluoro-pyridin-4-yl)-(indol-1-yl)-propylamine hydrochloride (75%) as a slightly yellow solid.

$^1$H-NMR (DMSO d$_6$, 300 MHz, TMS) [δ, ppm]: 0.9 (t, 3H, CH$_3$), 1.65 (m, 2H, CH$_2$), 4.0 (dm, 2H, NCH$_2$), 6.35 (t, 1H, arom.), 6.7 (d, 1H, arom.), 7.2 (m, 2H, arom.), 7.4 (d, 1H, arom.), 7.65 (d, 1H, arom.), 7.7 (d, 1H, arom.), 8.25 (d, 1H, arom.), 8.9 (d, 1H, arom.)

MS (CI+): 270 [M$^+$+H, free base]

Example 11

3-Methyl-N-(propylidene)-1H-indol-1-amine

Prepare a solution of 44.7 kg (398 mol) potassium tert-butoxide in 80 kg N-methylpyrrolidone (NMP). Additionally prepare a solution of 21.5 kg (190 mol) hydroxylamine-O-sulfonic acid (HOSA) in 98 kg NMP, and cool the HOSA-solution after a clear liquid is obtained to 10° C.

A solution of 10 kg (76.2 mol) 3-methylindole in 50 kg NMP is prepared, and add an initial amount of 0.08–0.12 eq. KOtBu-solution to the 3-methylindole solution. The HOSA and the KOtBu solutions are added over a period of 120 min simultaneously and proportionally over mass flow meters at 20° C. to the reaction mixture. After the addition is completed, add to the resulting dark brown suspension 6.9 L (381 mol) water, 13.7 kg (228.6 mol) acetic acid (100%) and 7.5 kg (129.2 mol) propionaldehyde. Stir the mixture at 20° C. for ~1 h, until completion of the reaction. The reaction mixture is then worked-up by adding 248 L water and 42 kg n-heptane. Unwanted salts precipitate from the reaction mixture. The resulting suspension is filtered and the phases are separated. The water phase is again extracted 3-times with 42 kg n-heptane. The combined organic phases are washed two times with 63 L water. The resulting brown heptane-solution is evaporated to dryness. This results in 11.6–12.5 kg 3-methyl-N-(propylidene)-1H-indol-1-amine (yield 81–90%) as a brown liquid.

bp. 121–123° C. (1 mbar)

$^1$H-NMR (300 MHz, DMSO-d$_6$, TMS) [δ, ppm]: 1.15 (t, 3H, CH$_3$), 2.3 (s, 3H, CH$_3$), 245 (m, 2H, CH$_2$), 7.05 (t, 1H, arom.), 7.2 (t, 1H, arom.), 7.5 (2 d, 2H, arom.), 7.8 (s, 1H, arom.), 8.05 (t, 1H, NCH). MS (CI+): 187 [M$^+$+H], 130 [M$^+$−NC$_3$H$_6$]

Example 12

3-Methyl-N-propyl-1H-indol-1-amine

In a 800 L vessel, prepare a solution of 3.0 kg (74.4 mol) sodium borohydride and 26.8 kg (124 mol, 86% purity) 3-methyl-N-(propylidene)-1H-indol-1-amine in 108 kg NMP. Prepare a solution of 4.5 kg (74.4 mol) glacial acetic acid in 27 kg NMP. Add the acetic acid solution over a period of about 30 nm at 30° C. to the sodium borohydride solution. Immediately hydrogen is evolved. Stir the reaction mixture at 30° C. until completion of the reaction (~1 h). Add 6.3 kg ethanol to the reaction mixture, foaming occurs immediately. The reaction mixture is then worked-up by adding additional 80 L water cautiously. Attention is taken during the addition of water such that foaming is controlled, slow addition of water is recommended especially in the beginning to avoid uncontrolled foaming. Care is taken to ensure no or only minimal foaming occurs while the first 1–2 L of water is added. The reaction mixture is allowed to stand over night. Extract the water phase three times with 45 kg n-heptane and wash the combined organic phases with 66 L water. Evaporate the combined organic phases to dryness. This results in 22.4 kg 3-methyl-N-propyl-1H-indol-1-amine (yield 90%, 94% purity) as a brown liquid.

$^1$H-NMR (300 MHz, DMSO d$_6$, TMS) [δ, ppm]: 0.9 (t, 3H, CH$_3$), 1.4 (m, 2H, CH$_2$), 2.2 (s 3H, CH$_3$), 2.95 (m, 2H, NCH$_2$), 6.3 (t, 1H, NH), 7.0 (t, 1H, arom.), 7.1 (t, 1H, arom.), 7.15 (s, 1H, arom.), 7.4 (d, 1H, arom.), 7.45 (d, 1H, arom.).

MS (CI+): 189 [M$^+$+H], 130 [M$^+$−NC$_3$H$_7$]

Example 13

3-Methyl-N-propyl-1H-indol-1-amine

Prepare a solution of sodium borohydride (4.54 kg, 120 mol) in 38 kg of NMP. Add to this solution, a solution of 3-methyl-N-(propylidene)-1H-indol-1-amine (38.6 kg, 190 mol) in 78 kg of n-heptane. Prepare a solution of 6.8 kg (120 mol) glacial acetic acid in 32 kg n-heptane. Add the acetic acid solution over a period of about 30 min at 30° C. to the sodium borohydride solution using a pump. Immediately hydrogen evolution occurs. Rinse the pump with 3 kg n-heptane and add the rinse to the reaction mixture. Stir the reaction mixture at 30° C. until completion of the reaction (~1 h). The reaction mixture is then worked-up by adding 76 L water. No or only minimal foaming is observed during the addition of water. Stir the mixture over night and separate the phases. Add 2.82 kg HCl (30%) and 4.75 kg water to the n-heptane phase, check the pH, if the pH is above 1, add more HCl. Heat this mixture to 75° C. internal temperature for ~2 h. Cool the mixture to 25° C. in order to control the evolution of hydrogen. If no more residual hydrogen is evolved, adjust pH level to 7, add additional 30 kg water, separate the phases and wash the n-Heptane phase twice with 37 kg water. Evaporate the n-heptane phase to dryness. This results in 37.5 kg 3-methyl-N-propyl-1H-indol-1-amine (98%) as a brown liquid.

Example 14

(3-Fluoropyridin-4-yl)-(3-methylindol-1-yl)-propylamine hydrochloride

Prepare a solution of 58.8 kg potassium tert-butoxide in 135.8 kg NMP, stir the suspension at 20° C. until a clear solution is obtained, which is designated as solution A.

Prepare a solution of 36.1 kg (175.6 mol) 3-methyl-N-propyl-1H-indol-1-amine and 24.3 kg (184.4 mol) 4-chloro-3-fluoropyridine in 68.5 kg NMP, which is designated as solution B.

Add both solutions A and B as prepared above simultaneously (~24 kg/h solution A and ~17.2 kg/h solution B) to a reactor, which is pre-filled with 15 kg NMP and 2 kg of solution A, while maintaining the internal temperature at −20° C. The volume of the liquids in the reaction vessel is maintained steady at the same level during the entire addition of solutions A and B by letting the mixed solution to another vessel. The reaction solution thus collected in another vessel is quenched with 19 kg water. After the complete amount of solutions A and B is added, wash the reactor with 20 kg NMP. For further work-up add 275 kg water and extract the basic water phase 4 times with 57 kg n-heptane. Extract the combined n-heptane phases twice with 175 kg water and 13.2 kg HCl (30%), separate the phases and add to the water phase 30.9 kg NaOH-solution (33%). Extract the water phase two times with 155 kg n-butyl acetate and wash the combined n-butyl acetate phase with 176 kg water. A sample of n-butyl acetate extract is taken to assay the free base. Based on the assay, dilute the n-butylacetate phase to contain about ten percent free base (w/w). Strip off the water under vacuum and add to the resulting n-butyl acetate phase 18.5 kg HCl (30%). Distill the mixture using a Dean-Stark trap to remove completely the water. During the distillation a solid precipitates. The suspension is cooled to 5° C. and filtered. Wash the filter cake twice with 76 kg n-butylacetate. After drying at 60–70° C., there remains 43.8 kg (3-fluoropyridin-4-yl)-(3-methylindol-1-yl)-propylamine hydrochloride (77.3%) as a slightly yellow solid.

mp. 219° C. (DSC, heating rate 5° C./min, loss of HCl and decomposition) $^1$H-NMR (300 MHz, DMSO-d$_6$, TMS) [δ, ppm]: 0.9 (t, 3H, CH$_3$), 1.7 (m, 2H, CH$_2$), 2.5. (m, 3H, CH$_3$), 4.0 (dm, 2H, CH$_2$), 6.3 (m, 1H, arom.), 7.2 (m, 2H, arom.), 7.3 (m, 1H, arom.), 7.4 (d, 1H, arom.), 7.7 (dd, 1H, arom.), 8.2 (d, 1H, arom.), 8.9 (d, 1H, arom.) MS (EI+, 70 eV): 283 [M+, free base], 240 [M+−$C_3H_7$], 130 [3-methylindole fragment], 96 [fluoropyridine fragment]

Example 15

4-Chloro-3-fluoropyridine

A 30-gal Hastelloy reactor under nitrogen is charged with 2.5 kg (25.8 mole) of 3-fluoropyridine, 3.4 kg (29.6 mole, 1.2 equiv.) of tetramethylethylenediamine (TMEDA) and 20 L of methyl tert-butyl ether (MTBE). The solution is cooled to −50° C. A total of 15.5 L (12.6 L, 29.6 mole, 1.15 equiv.) of 1.9 M lithium diisopropylamide (IDA) solution (heptane/THF/ethylbenzene) is added over a period of 24 min while maintaining a temperature of −40 to −48° C. The light-brown suspension is stirred for 50 min at −44 to −48° C. A solution of 7 kg (29.6 mole, 1.15 equiv.) of hexachloroethane in 20 L of MTBE is added over a period of 48 min while maintaining a temperature of −40 to −46° C. After stirring for 20 min at −40° C., the reaction is warmed to 0° C., then quenched into a reactor that contained 54 L of cold water. After stirring at 20–25° C. for 20 min, the mixture is filtered through Celite to break a minor emulsion. The layers are separated. The aqueous layer is extracted with 5 L of MTBE. The organic layers are combined, then extracted with portions (1×21 L, 3×13 L) of 2 N HCl. The acidic aqueous phases are combined, partitioned with 16 L of MTBE, then basified to pH 6.19 by adding 6.5 kg of 50% NaOH while maintaining a temperature of 15–20° C. The layers are separated. The aqueous phase is extracted with 10 L of MTBE. The combined organic phase is dried over 3.0 kg of sodium sulfate, then filtered and concentrated (56° C., 575 mbar during most of the concentration, 400 mbar for final concentration) to give 3.7 kg of 4-chloro-3-fluoropyridine, as a brown liquid, 2.4 kg corrected for 31.2% solvent by NMR and 95.5% purity by HPLC, 70.2% yield.

Example 16

(3-Fluoropyridin-4-yl)-(3-methylindol-1-yl)-propylamine hydrochloride

Prepare a solution of 510 g (4.5 mol) potassium tert-butoxide in 1190 g NMP, stir the suspension at 20° C. until a clear solution is obtained (Solution A).

Prepare a solution of 154.1 g (769 mmol, 94% purity) 3-methyl-N-propyl-1H-indol-1-amine, 112.7 g (846 mmol, 99% purity) 4-chloro-3-fluoropyridine and 622 g NMP (Solution B).

Fill the loop system with 950 g of solution A, which is connected to a continuous stirred tank reactor (CSTR) and a static mixer with a loop pump. Cool the loop system to −15° C. Start charging solution A into the CSTR and solution B from the static mixer, add both solutions for 53 min under temperature control (−15° C.). During the addition hold the volume in the CSTR constant at approx. 360 mL. The reaction mixture is quenched with 247 g water. After the end of the charge drain the loop system and rinse the system with 951 g water. Add to the rinse and the quenched reaction solution additional 1224 g water. Extract the water phase four times with 380 g n-heptane. Extract the resulting n-heptane phase twice with a solution of 771 g water and 45.4 g HCl (37%). Add to the resulting water phase 131 g NaOH (33%) and extract twice with 680 g n-butylacetate. Wash the resulting n-butylacetate phase once with 775 g water. Add 79.6 g HCl (37%) and distill the resulting mixture using a Dean-Stark trap under vacuum, until no more water is removed. As the product begins to crystallize, cool the reaction mixture to 5° C., and filter the product. Dry under vacuum in a tray dryer. This results in 164.4 g 3-fluoropyridin-4-yl-(3-methylindol-1 yl)-propylamine hydrochloride (yield 71%).

Example 17

N-(propylidene)-1H-indol-1-amine

Prepare a solution of 26.8 kg (239 mol) potassium tert-butoxide (KOtBu) in 50 kg N-methylpyrrolidone (NMP). Additionally prepare a solution of 13.8 kg (120 mol) hydroxylamine-O-sulfonic acid (HOSA) in 71 kg NMP, and cool the HOSA-solution after a clear liquid is obtained to 10° C.

Prepare a solution of 6.4 kg (54.6 mol) indole in 25 kg NMP. Add to this solution the HOSA and the KOtBu solutions as prepared above over a period of 180 min simultaneously and proportionally over mass flow meters and maintain the reaction mixture at 15° C. After the addition is completed, add to the resulting dark brown suspension 4.3 L (239 mol) water, 9.7 kg (161.5 mol) acetic acid (100%) and 5.3 kg (91.3 mol) propionaldehyde. Stir the mixture at 20° C. for ~1 h, until completion of the reaction. The reaction mixture is then worked-up by adding 180 L water and 21 kg n-heptane. Unwanted salts precipitate from the reaction mixture. The resulting suspension is filtered and the phases are separated. The water phase is again extracted 4-times with 21 kg n-heptane. The combined organic phases are washed two times with 45 L water. The resulting brown heptane-solution is evaporated to a 15–25% solution. This results in 6.3–7.0 kg N-(propylidene)-1H-indol-1-amine (yield 67–74%, corrected for 19.7–24.1% assay) as a brown liquid.

$^1$H-NMR (400 MHz, DMSO-$d_6$, TMS) [δ, ppm]: 1.19 (t, 3H, $CH_3$), 2.48 (m, 2H, $CH_2$), 6.60 (d, 1H, arom) 7.08 (t, 1H, arom.), 7.22 (t, 1H, arom.), 7.57 (d, 1H, arom.), 7.61 (d, 1H, arom.), 8.03 (d, 1H, arom), 8.19 (t, 1H, NCH). MS (ES+): 173 [M++H], 117 [M+−$NC_3H_6$]

Example 18

N-propyl-1H-indol-1-amine

Prepare a solution of 0.83 kg (21.9 mol) sodium borohydride in 16.6 kg NMP. Add 31.9 kg N-(propylidene)-1H-indol-1-amine as a 19.7% solution in n-heptane (36.5 mol) and additional 7.7 kg n-Heptane. Prepare a solution of 1.32 kg (21.9 mol) glacial acetic acid in 2.8 kg n-heptane. Add the acetic acid solution over a period of about 30 min at 30° C. to the sodium borohydride solution using a pump. Immediately hydrogen evolution will occur. Rinse the pump with 2 kg n-heptane. Stir the reaction mixture at 30° C. until completion of the reaction (~1 h). The reaction mixture is then worked-up by adding 20 L water. No or only minimal foaming is observed during the addition of water. Stir the mixture over night and separate the phases. Add 0.9 kg HCl (30%) and 3.4 kg water to the n-heptane phase, check whether the pH is below 1. Add additional amounts of HCl if necessary to adjust the pH around 1. Heat this mixture to 75° C. internal temperature for ~2 h. Cool the mixture to 25° C. in order to control the residual hydrogen that is evolved. If no more residual hydrogen is evolved, add additional 20.3 kg water, and adjust pH to a level >7 with NaOH (33%).

Separate the phases and wash the n-heptane phase with 20.3 kg water. Evaporate the n-heptane phase to dryness. This results in 5.84 kg N-propyl-1H-indol-1-amine (82.6%) as a brown liquid.

$^1$H-NMR (400 MHz, DMSO-d$_6$, TMS) [δ, ppm]: 0.91 (t, 3H, CH$_3$), 1.35 (m, 2H, CH$_2$), 3.00 (m, 2H, CH$_2$), 6.33 (d, 1H, arom), 6.43 (t, 1H, NH) 7.12 (t, 1H, arom.), 6.98 (t, 1H, arom.), 7.35 (d, H, arom.), 7.46 (d, 1H, arom.), 7.50 (d, 1H, arom.). MS (ES+): 175 [M$^+$+H]

Example 19

Indol-1-yl-propyl-pyridin-4-yl-amine hydrochloride

Prepare a solution of 12.4 kg (110.7 mol) potassium tert-butoxide in 23.6 kg NMP, stir the suspension at 20° C. until a clear solution is obtained (Solution A).

Prepare a second solution of 5.84 kg (27.7 mol, assay 82.6%) N-propyl-1H-indol-1-amine and 4.36 kg (29.1 mol) 4-chloropyridine hydrochloride in 15 kg NMP (Solution B).

Add solution A to solution B while maintaining the temperature at 20° C. Stir for 1 h and check for completion of reaction. The reaction mixture is quenched in 135 kg water. Adjust pH value of the solution to about 2 with HCl (30%) and extract with 20 kg n-heptane twice. Discard organic layer. Adjust pH value of the aqueous layer to 12 with NaOH (33%) and extract with 16 kg n-butylacetate twice. Discard aqueous layer. Wash organic layer with 23 kg of water. Add 10.8 kg methanolic HCl (29.9 mol, assay 10.1%) to the organic layer at 20° C. After crystallization cool the mixture to 5° C., filter the product and wash with n-butylacetate. Dry under vacuum at 80° C. in a tray dryer. This will result in 5.8 kg indol-1-yl-propyl-pyridin-4-yl-amine hydrochloride (yield 73%) as a white to beige solid.

$^1$H-NMR (400 MHz, DMSO-d$_6$, TMS) [δ, ppm]: 0.94 (t, 3H, CH$_3$), 1.62 (m, 2H, CH$_2$), 4.05 (dm, 2H, CH$_2$), 6.74 (d, 1H, arom.), 7.19 (m, 1H, arom.), 7.28 (m, 1H, arom.), 7.30 (d, 1H, arom.), 5.8–7.6 (s v br, 2H, arom.), 7.63 (d, 1H, arom.), 7.70 (d, 1H, arom.), 8.43 (d br, 2H, arom.), 15.2 (s br, 1H, NH$^+$). MS (ES+): 252 [M$^+$+H, free base].

The following example illustrates the N-amination product obtained by following the procedures set forth in EP 0 249 452.

Comparative Example 1

1H-indol-1-amine

A solution of 3.3 g (3.2 g corrected for 97% purity) of hydroxylamine-O-sulfonic acid (HOSA) in 7.7 g of water is prepared and chilled to 0–5° C. An amination vessel is charged with 10.0 g indole and 50.0 g of water. The HOSA/water solution and 7.3 mL of 30% NaOH solution are then simultaneously metered into the amination vessel over a period of 120 minutes while maintaining a reaction temperature of 20–25° C. HPLC analysis shows that no 1H-indol-1-amine is formed.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A process for the preparation of a compound of the formula II:

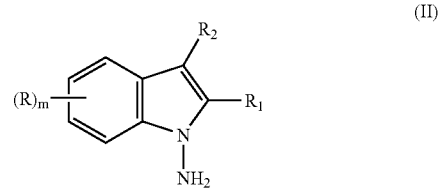

which consists essentially the steps of:
(a) preparing a solution of hydroxylamine-O-sulfonic acid in a suitable organic solvent;
(b) preparing a solution of a suitable base in a suitable organic solvent;
(c) preparing a solution of a compound of the formula I in a suitable organic solvent;

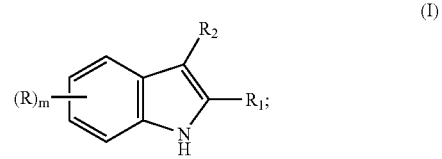

(d) contacting simultaneously and proportionally said solution from said step (a) and said solution from said step (b) with said solution from step (c) taken in a suitable reaction vessel at a suitable reaction temperature to provide said compound of formula (II) in high purity and high yields;

wherein

R is hydrogen, $C_1$–$C_4$-alkyl, $C_1$–$C_4$-alkoxy, benzyloxy or fluoroalkyl or fluoroalkoxy of the formula $C_nH_xF_y$ or $OC_nH_xF_y$, wherein n is an integer from 1 to 4, x is an integer from 0 to 8, y is an integer from 1 to 9 and sum of x and y is 2n+1;

$R_1$ and $R_2$ are the same or different and are each independently selected from hydrogen, $C_1$–$C_4$-alkyl, $C_1$–$C_4$-alkoxy, benzyloxy or fluoroalkyl or fluoroalkoxy of the formula $C_nH_xF_y$ or $OC_nH_xF_y$, wherein n is an integer from 1 to 4, x is an integer from 0 to 8, y is an integer from 1 to 9 and sum of x and y is 2n+1; or $R_1$ and $R_2$ taken together with the carbon atoms to which they are attached form a $C_5$–$C_8$cyclic ring; and m is 1 or 2.

2. The process according to claim 1 wherein said solvent in said steps (a) and (b) is an aprotic solvent.

3. The process according to claim 2 wherein said aprotic solvent is N-methylpyrrolidinone.

4. The process according to claim 2 wherein said solvent is N,N-dimethylformamide.

5. The process according to claim 2 wherein said solvent is N,N-dimethylacetamide.

6. The process according to claim 1 wherein said base in said step (b) is an organic base.

7. The process according to claim 6 wherein said base is having an pK$_a$ value at least about the same as that of indole.

8. The process according to claim 6 wherein said organic base is an alkaline metal alkoxide.

9. The process according to claim 8 wherein said alkaline metal alkoxide is selected from the group consisting of lithium methoxide, lithium ethoxide, lithium isopropoxide, lithium tert-butoxide, sodium methoxide, sodium ethoxide, sodium isopropoxide, sodium tert-butoxide, potassium methoxide, potassium ethoxide, potassium isopropoxide, potassium tert-butoxide, cesium methoxide, cesium ethoxide, cesium isopropoxide and cesium tert-butoxide.

10. The process according to claim 8 wherein said alkaline metal alkoxide is potassium tert-butoxide.

11. The process according to claim 1 wherein said solvent in said step (c) is an aprotic solvent.

12. The process according to claim 11 wherein said aprotic solvent is N-methylpyrrolidinone.

13. The process according to claim 11 wherein said aprotic solvent is N,N-dimethylformamide.

14. The process according to claim 11 wherein said aprotic solvent is dimethyl acetamide.

15. The process according to claim 1 wherein said reaction temperature is from about $-5°$ C. to about $40°$ C.

16. The process according to claim 1 wherein said reaction temperature is from about $0°$ C. to about $25°$ C.

17. The process according to claim 1 wherein said base is present in an amount of from about 1 mole to about 10 moles with reference to said compound of formula I.

18. The process according to claim 1 wherein said base is present in an amount of from about 3 mole to about 6 moles with reference to said compound of formula I.

19. The process according to claim 1 wherein said contacting in said step (d) is affected by means of a static mixing.

20. The process according to claim 1 wherein said contacting in said step (d) is affected by means of a continuous reactor.

21. The process according to claim 1 wherein said contacting in said step (d) is affected in a batch reactor.

22. The process according to claim 1 wherein R and $R_1$ are hydrogen and $R_2$ is methyl.

23. The process according to claim 1 wherein $R_1$ and $R_2$ taken together with the carbon atoms to which they are attached form a benzene ring.

24. A process for the preparation of a compound of the formula II:

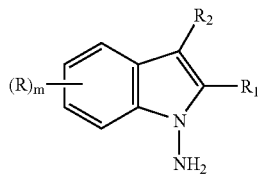

(II)

which consists essentially the steps of:
(a) preparing a solution of hydroxylamine-O-sulfonic acid and a compound of the formula I:

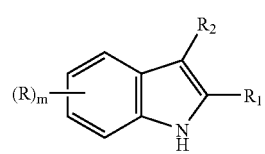

(I)

in a suitable organic solvent;

(b) preparing a solution of a suitable base in a suitable organic solvent;

(c) contacting simultaneously and proportionally said solution from said step (a) with said solution from said step (b) at a suitable reaction temperature to provide said compound of formula (II) in high purity and high yields;

wherein

R is hydrogen, $C_1$–$C_4$-alkyl, $C_1$–$C_4$-alkoxy, benzyloxy or fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and sum of x and y is 2n+1;

$R_1$ and $R_2$ are the same or different and are each independently selected from hydrogen, $C_1$–$C_4$-alkyl, $C_1$–$C_4$-alkoxy, benzyloxy or fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and sum of x and y is 2n+1; or $R_1$ and $R_2$ taken together with the carbon atoms to which they are attached form a $C_5$–$C_8$ cyclic ring; and m is 1 or 2.

25. A process for the preparation of a compound of the formula IV:

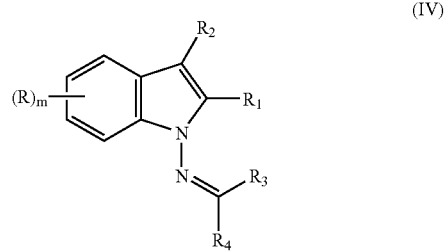

(IV)

which comprises:
adding simultaneously and proportionally a solution of hydroxylamine-O-sulfonic acid in a suitable organic solvent and a solution of a suitable base in a suitable organic solvent to a solution of a compound of the formula I in a suitable organic solvent at a suitable reaction temperature wherein said compound of the formula (I) is taken in a suitable reaction vessel,

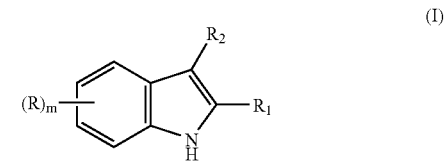

(I)

to provide a compound of the formula (II):

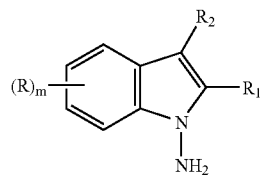

and reacting said compound of formula (II) in said reaction vessel with a compound of the formula (III):

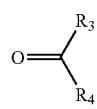

to provide the compound of formula (IV):
wherein
R is hydrogen, $C_1$–$C_4$-alkyl, $C_1$–$C_4$-alkoxy, benzyloxy or fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and sum of x and y is 2n+1;
$R_1$ and $R_2$ are the same or different and are each independently selected from hydrogen, $C_1$–$C_4$-alkyl, $C_1$–$C_4$-alkoxy, benzyloxy or fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and sum of x and y is 2n+1;
$R_3$ and $R_4$ are the same or different and are each independently selected from hydrogen or $C_1$–$C_4$-alkyl; and
m is 1 or 2.

26. The process according to claim 25 wherein said solvent is an aprotic solvent.

27. The process according to claim 26 wherein said aprotic solvent is N-methylpyrrolidinone.

28. The process according to claim 26 wherein said aprotic solvent is N,N-dimethylformamide.

29. The process according to claim 26 wherein said aprotic solvent is N,N-dimethylacetamide.

30. The process according to claim 25 wherein said base is an organic base.

31. The process according to claim 30 wherein said organic base is an alkaline metal alkoxide.

32. The process according to claim 31 wherein said alkaline metal alkoxide is selected from the group consisting of lithium methoxide, lithium ethoxide, lithium isopropoxide, lithium tert-butoxide, sodium methoxide, sodium ethoxide, sodium isopropoxide, sodium tert-butoxide, potassium methoxide, potassium ethoxide, potassium isopropoxide, potassium tert-butoxide, cesium methoxide, cesium ethoxide, cesium isopropoxide and cesium tert-butoxide.

33. The process according to claim 31 wherein said alkaline metal alkoxide is potassium tert-butoxide.

34. The process according to claim 25 wherein said reaction temperature is from about −5° C. to about 40° C.

35. The process according to claim 25 wherein said reaction temperature is from about 0° C. to about 25° C.

36. The process according to claim 25 wherein said base is present in an amount of from about 1 mole to about 10 moles with reference to said compound of formula I.

37. The process according to claim 25 wherein said base is present an amount of from about 3 mole to about 6 moles with reference to said compound of formula I.

38. The process according to claim 25 wherein R, $R_1$ and $R_4$ are hydrogen, $R_2$ is methyl and $R_3$ is ethyl.

39. A process for the preparation of a compound of the formula VI or a suitable salt thereof:

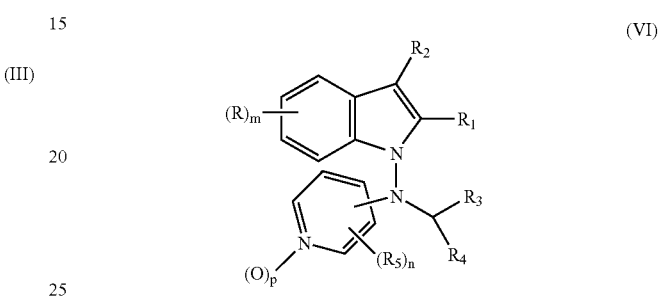

which comprises the steps of:
(a) adding simultaneously and proportionally a solution of hydroxylamine-O-sulfonic acid in a suitable organic solvent and a solution of a suitable base in a suitable organic solvent to a solution of a compound of the formula I in a suitable organic solvent at a suitable reaction temperature wherein said compound of the formula (I) is taken in a suitable reaction vessel,

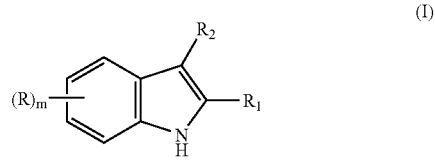

to provide a compound of the formula (II):

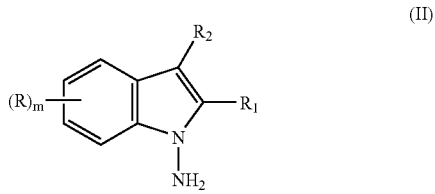

and reacting said compound of formula (III) in said reaction vessel with a compound of the formula (III):

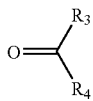
(III)

to provide a compound of formula (IV):

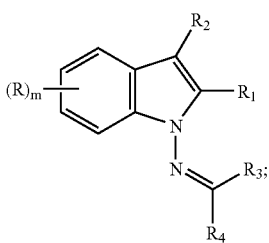
(IV)

(b) reacting said compound of formula (IV) with a suitable reducing agent to provide a compound of formula (V):

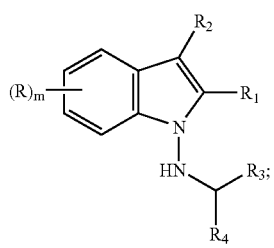
(V)

(c) reacting said compound of formula (V) with a compound of the formula (VII):

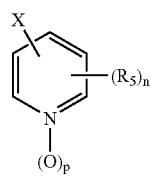
(VII)

in the presence of a suitable base in a suitable organic solvent to provide the compound of formula (VI), which is optionally reacted with a suitable inorganic acid to provide a salt of the compound of formula (VI);
wherein
R is hydrogen, $C_1$–$C_4$-alkyl, $C_1$–$C_4$-alkoxy, benzyloxy or fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and sum of x and y is 2n+1;
$R_1$ and $R_2$ are the same or different and are each independently selected from hydrogen, $C_1$–$C_4$-alkyl, $C_1$–$C_4$-alkoxy, benzyloxy or fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and sum of x and y is 2n+1; or
$R_3$ and $R_4$ are the same or different and are each independently selected from hydrogen or $C_1$–$C_4$-alkyl; and m is 1 or 2;
$R_5$ is hydrogen, nitro, amino, halogen, $C_{1-4}$-alkyl, $C_{1-4}$-alkanoylamino, phenyl-$C_{1-4}$-alkanoylamino, phenylcarbonylamino, alkylamino or phenyl-$C_{1-4}$-alkylamino;
X is halogen;
m and n are 1 or 2 and p is 0 or 1.

40. The process according to claim 39 wherein said reducing agent in said step (b) is sodium borohydride.

41. The process according to claim 39 wherein said reaction in said step (b) is carried out in a suitable organic solvent.

42. The process according to claim 41 wherein said solvent is an aprotic solvent.

43. The process according to claim 41 wherein said solvent is N-methylpyrrolidinone, N,N-dimethylformamide, dimethyl acetamide, tetrahydrofuran, heptane, hexane, toluene, petroleum ether or a mixture thereof.

44. The process according to claim 41 wherein said solvent is N-methylpyrrolidinone or a mixture of N-methylpyrrolidinone and n-heptane.

45. The process according to claim 39 wherein said reaction temperature in said step (a) is in the range of from about –70° C. to about 150° C.

46. The process according to claim 39 wherein said reaction temperature in said step (a) is in the range of from about –20° C. to about 15° C.

47. The process according to claim 39 wherein said base in said step (c) is potassium tert-butoxide.

48. The process according to claim 39 wherein said step (c) is performed by means of a static mixer.

49. The process according to claim 39 wherein said step (c) is performed in a continuous stirred tank reactor.

50. The process according to claim 39 wherein said step (c) is performed in a batch reactor.

51. The process according to claim 39 wherein said step (c) is performed in a micro-reactor.

52. The process according to claim 39 wherein said step (c) is performed in a continuous stirred tank reactor combined with static mixers in a loop system.

53. A compound of the formula (IV):

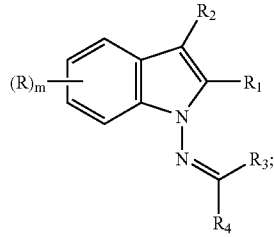
(IV)

wherein R is $C_1$–$C_4$-alkoxy or benzyloxy; $R_1$ and $R_3$ are hydrogen;
$R_2$ is methyl or hydrogen; and $R_4$ is $C_1$–$C_4$-alkyl; and m is 1 or 2; or an enantiomer, a stereoisomer or a mixture there of, a tautomer thereof, or a pharmaceutically acceptable salt, a solvate or a derivative thereof.

54. The compound according to claim 53 which is selected from the group consisting of:
5-benzyloxy-N-(propylidene)-1H-indol-1-amine; and
5-methoxy-N-(propylidene)-1H-indol-1-amine.

* * * * *